(12) United States Patent
Plahey et al.

(10) Patent No.: US 8,926,550 B2
(45) Date of Patent: Jan. 6, 2015

(54) DATA COMMUNICATION SYSTEM FOR PERITONEAL DIALYSIS MACHINE

(75) Inventors: Kulwinder S. Plahey, Martinez, CA (US); Tri Ly, Dublin, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1147 days.

(21) Appl. No.: 11/515,360

(22) Filed: Aug. 31, 2006

(65) Prior Publication Data
US 2008/0097283 A1 Apr. 24, 2008

(51) Int. Cl.
A61M 1/00 (2006.01)
A61M 1/28 (2006.01)

(52) U.S. Cl.
CPC ......... *A61M 1/28* (2013.01); *A61M 2205/3569* (2013.01); *A61M 2205/52* (2013.01); *A61M 2205/6018* (2013.01)
USPC ............................................. 604/29; 604/131

(58) Field of Classification Search
USPC .......... 604/29, 131, 151, 890.1; 600/431, 432
See application file for complete search history.

(56) References Cited

U.S. PATENT DOCUMENTS

| | | | |
|---|---|---|---|
| 4,676,467 A | 6/1987 | Palsulich | |
| 4,778,451 A | 10/1988 | Kamen | |
| 4,808,161 A | 2/1989 | Kamen | |
| 4,826,482 A | 5/1989 | Kamen | |
| 4,902,282 A | 2/1990 | Bellotti et al. | |
| 4,950,134 A | 8/1990 | Bailey et al. | |
| 4,976,162 A | 12/1990 | Kamen | |
| 5,002,471 A | 3/1991 | Perlov | |
| 5,088,515 A | 2/1992 | Kamen | |
| 5,116,021 A | 5/1992 | Faust et al. | |
| 5,146,713 A | 9/1992 | Grafius | |
| 5,178,182 A | 1/1993 | Kamen | |
| 5,193,990 A | 3/1993 | Kamen et al. | |
| 5,211,201 A | 5/1993 | Kamen et al. | |
| 5,241,985 A | 9/1993 | Faust et al. | |
| 5,324,422 A | 6/1994 | Colleran et al. | |
| 5,350,357 A | 9/1994 | Kamen et al. | |
| D351,470 S | 10/1994 | Scherer et al. | |
| 5,353,837 A | 10/1994 | Faust | |
| 5,395,351 A | 3/1995 | Munsch | |
| 5,421,208 A | 6/1995 | Packard et al. | |
| 5,421,823 A | 6/1995 | Kamen et al. | |
| 5,431,626 A | 7/1995 | Bryant et al. | |

(Continued)

FOREIGN PATENT DOCUMENTS

| | | | |
|---|---|---|---|
| CN | 1146728 | 4/1997 | ................ A61J 1/16 |
| CN | 1593677 | 3/2005 | ............... A61M 1/28 |

(Continued)

OTHER PUBLICATIONS

Gambro®, "Prismaflex™ Anticipating Critical Care needs and taking our innovative response . . . to new heights," © 2004, Gambro Inc., Lakewood, CO, 8 pp.

(Continued)

*Primary Examiner* — Kevin C Sirmons
*Assistant Examiner* — Phillip Gray
(74) *Attorney, Agent, or Firm* — Fish & Richardson P.C.

(57) ABSTRACT

A portable peritoneal dialysis apparatus having a USB interface for uploading and downloading patient files and records using a USB flash drive, and for playing a training video for the PD machine on the machine's own display, transferred via a USB flash drive.

10 Claims, 2 Drawing Sheets

(56) References Cited

U.S. PATENT DOCUMENTS

| | | | |
|---|---|---|---|
| 5,438,510 A | 8/1995 | Bryant et al. | |
| 5,445,610 A * | 8/1995 | Evert | 604/29 |
| 5,447,286 A | 9/1995 | Kamen et al. | |
| 5,474,683 A | 12/1995 | Bryant et al. | |
| 5,486,286 A | 1/1996 | Peterson et al. | |
| 5,570,716 A | 11/1996 | Kamen et al. | |
| 5,628,908 A | 5/1997 | Kamen et al. | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |
| 5,713,865 A | 2/1998 | Manning et al. | |
| 5,741,125 A | 4/1998 | Neftel et al. | |
| 5,755,683 A | 5/1998 | Houle et al. | |
| 5,771,914 A | 6/1998 | Ling et al. | |
| 5,772,637 A | 6/1998 | Heinzmann et al. | |
| 5,938,634 A | 8/1999 | Packard | |
| 5,989,423 A | 11/1999 | Kamen | |
| 6,036,680 A | 3/2000 | Horne et al. | |
| 6,041,801 A | 3/2000 | Gray et al. | |
| 6,065,941 A | 5/2000 | Gray et al. | |
| 6,074,359 A | 6/2000 | Keshaviah et al. | |
| 6,118,207 A | 9/2000 | Ormerod et al. | |
| 6,164,621 A | 12/2000 | Bouchard et al. | |
| 6,165,154 A | 12/2000 | Gray et al. | |
| 6,220,295 B1 | 4/2001 | Bouchard et al. | |
| 6,223,130 B1 | 4/2001 | Gray et al. | |
| 6,316,864 B1 | 11/2001 | Ormerod | |
| 6,343,614 B1 | 2/2002 | Gray et al. | |
| 6,364,857 B1 | 4/2002 | Gray et al. | |
| 6,382,923 B1 | 5/2002 | Gray | |
| 6,406,276 B1 | 6/2002 | Normand et al. | |
| 6,416,293 B1 | 7/2002 | Bouchard et al. | |
| 6,497,676 B1 | 12/2002 | Childers et al. | |
| 6,503,062 B1 | 1/2003 | Gray et al. | |
| 6,520,747 B2 | 2/2003 | Gray et al. | |
| 6,558,343 B1 | 5/2003 | Neftel | |
| 6,592,542 B2 | 7/2003 | Childers et al. | |
| 6,604,908 B1 | 8/2003 | Bryant et al. | |
| 6,663,359 B2 | 12/2003 | Gray | |
| 6,709,417 B1 | 3/2004 | Houle et al. | |
| 6,726,656 B2 | 4/2004 | Kamen et al. | |
| 6,744,350 B2 * | 6/2004 | Blomquist | 604/890.1 |
| 6,746,514 B2 | 6/2004 | Bedingfield et al. | |
| 6,749,403 B2 | 6/2004 | Bryant et al. | |
| 6,764,761 B2 | 7/2004 | Eu et al. | |
| 6,808,369 B2 | 10/2004 | Gray et al. | |
| 6,814,547 B2 | 11/2004 | Childers et al. | |
| 6,929,751 B2 | 8/2005 | Bowman, Jr. et al. | |
| 7,083,719 B2 | 8/2006 | Bowman, Jr. et al. | |
| 7,162,306 B2 * | 1/2007 | Caby et al. | 607/60 |
| 7,263,710 B1 * | 8/2007 | Hummel et al. | 600/300 |
| 2002/0107474 A1 | 8/2002 | Noack | |
| 2002/0147423 A1 | 10/2002 | Burbank et al. | |
| 2003/0018395 A1 | 1/2003 | Crnkovich et al. | |
| 2003/0029451 A1 | 2/2003 | Blair et al. | |
| 2003/0130606 A1 * | 7/2003 | Tuck | 604/4.01 |
| 2003/0136189 A1 | 7/2003 | Lauman et al. | |
| 2003/0200812 A1 | 10/2003 | Kuhn et al. | |
| 2003/0204162 A1 | 10/2003 | Childers et al. | |
| 2003/0217957 A1 | 11/2003 | Bowman et al. | |
| 2003/0217961 A1 | 11/2003 | Hopping | |
| 2003/0217975 A1 | 11/2003 | Yu et al. | |
| 2003/0218623 A1 | 11/2003 | Krensky et al. | |
| 2003/0220599 A1 | 11/2003 | Lundtveit et al. | |
| 2003/0220605 A1 | 11/2003 | Bowman et al. | |
| 2003/0220607 A1 | 11/2003 | Busby et al. | |
| 2003/0220608 A1 | 11/2003 | Huitt et al. | |
| 2003/0220609 A1 | 11/2003 | Childers et al. | |
| 2004/0010223 A1 | 1/2004 | Busby et al. | |
| 2004/0019313 A1 | 1/2004 | Childers et al. | |
| 2004/0019320 A1 | 1/2004 | Childers et al. | |
| 2004/0031756 A1 * | 2/2004 | Suzuki et al. | 604/29 |
| 2004/0064080 A1 | 4/2004 | Cruz et al. | |
| 2004/0067161 A1 | 4/2004 | Axelsson | |
| 2004/0082903 A1 | 4/2004 | Micheli | |
| 2004/0122353 A1 * | 6/2004 | Shahmirian et al. | 604/65 |
| 2004/0135078 A1 | 7/2004 | Mandro et al. | |
| 2005/0131332 A1 | 6/2005 | Kelly et al. | |
| 2005/0151422 A1 * | 7/2005 | Gilmour | 307/10.1 |
| 2005/0230292 A1 | 10/2005 | Beden et al. | |
| 2005/0234381 A1 | 10/2005 | Niemetz et al. | |
| 2005/0242034 A1 * | 11/2005 | Connell et al. | 210/646 |
| 2006/0234381 A1 * | 10/2006 | Schwalbe et al. | 436/34 |
| 2011/0004351 A1 | 1/2011 | Kelly et al. | |

FOREIGN PATENT DOCUMENTS

| | | | |
|---|---|---|---|
| JP | 2001-229292 | 8/2001 | |
| JP | 2003-047657 | 2/2003 | |
| JP | 2003047657 | 2/2003 | |
| JP | 2004-057284 | 2/2004 | |
| JP | 2005-245669 | 9/2005 | |
| WO | 96/24396 | 8/1996 | A61M 1/28 |
| WO | WO0164263 A1 | 9/2001 | |
| WO | WO 02/34314 | 5/2002 | |
| WO | WO2005035023 A1 | 4/2005 | |
| WO | WO2005044339 A3 | 5/2005 | |

OTHER PUBLICATIONS

Gambro®, "DEHP-Free Cartridge Blood Sets," © Nov. 2004, Gambro, Inc., Lakewood, CO, 4 pp.

International Search Report and Written Opinion of the International Searching Authority, or the Declaration dated Feb. 1, 2008 for International Application No. PCT/US2007/077113.

Notification Concerning Transmittal of International Preliminary Report on Patentability dated Mar. 12, 2009 for International Application No. PCT/US2007/077113.

* cited by examiner

DATA COMMUNICATION SYSTEM FOR PERITONEAL DIALYSIS MACHINE

BACKGROUND OF THE INVENTION

The present invention relates generally to apparatus for the treatment of end stage renal disease. More specifically, the present invention relates to portable apparatus for the performance of peritoneal dialysis.

Dialysis to support a patient whose renal function has decreased to the point where the kidneys no longer sufficiently function is well known. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because the treatment is extracorporeal, it requires special machinery and a visit to a center, such as in a hospital, that performs the treatment.

To overcome this disadvantage associated with hemodialysis, peritoneal dialysis (hereafter "PD") was developed. PD utilizes the patient's own peritoneum (a membranous lining of the abdominal body cavity) as a semi-permeable membrane. With its good perfusion, the peritoneum is capable of acting as a natural semi-permeable membrane.

PD periodically infuses sterile aqueous solution into the peritoneal cavity. This aqueous solution is called PD solution, or dialysate for short. Diffusion and osmosis exchanges take place between the solution and the blood stream across the peritoneum. These exchanges remove the waste products that the kidneys normally excrete. The waste products typically consist of solutes like urea and creatinine. The kidneys also function to maintain the proper levels of other substances, such as sodium and water, which also need to be regulated by dialysis. The diffusion of water and solutes across the peritoneal membrane during dialysis is called ultrafiltration.

In continuous ambulatory PD, a dialysis solution is introduced into the peritoneal cavity utilizing a catheter, normally placed into position by a visit to a doctor. An exchange of solutes between the dialysate and the blood is achieved by diffusion.

In many prior art PD machines, removal of fluids is achieved by providing a suitable osmotic gradient from the blood to the dialysate to permit water outflow from the blood. This allows a proper acid-base, electrolyte and fluid balance to be achieved in the body. The dialysis solution is simply drained from the body cavity through the catheter. The rate of fluid removal is dictated by height differential between patient and machine.

A preferred PD machine is one that is automated. These machines are called cyclers, designed to automatically infuse, dwell, and drain PD solution to and from the patient's peritoneal cavity. A cycler is particularly attractive to a PD patient because it can be used at night while the patient is asleep. This frees the patient from the day-to-day demands of continuous ambulatory PD during his/her waking and working hours.

The treatment typically lasts for several hours. It often begins with an initial drain cycle to empty the peritoneal cavity of spent dialysate. The sequence then proceeds through a succession of fill, dwell, and drain phases that follow one after the other. Each phase is called a cycle.

The intent of this invention is to provide improved data communications for a PD cycler.

SUMMARY OF THE INVENTION

In one aspect the peritoneal dialysis machine, according to the invention, comprises a controller for directing the sequence of operations on PD cycler to carry out peritoneal dialysis on the patient, together with a USB data communications interface including a USB port on the machine that accepts a USB flash drive, and a USB interface control system for managing the uploading and downloading of peritoneal dialysis related data, such as a digital record of therapy data following a treatment, a patient profile and prescription, and a training video for the same machine playable on the machine's display using a built in media player.

In another aspect the invention comprises a method of communicating with a PD machine by providing a USB interface including a USB port on the machine, and using a USB flash drive inserted in the port either uploading patient data to the machine by transferring patient data to a USB flash drive and inserting the user's USB flash drive in the port or downloading treatment data to the user by transferring treatment data to a USB controller and inserting the user's USB flash drive in the port and then transferring the data onto the user's USB flash drive for transfer to a PC.

In a further aspect the invention comprises playing a training video on the PD machine provided via the user's USB flash drive using the USB interface to transfer the file and a built in media player to play the training video on the PD machine's own display screen.

The details of one or more embodiments of the invention are set forth in the accompanying drawings and the description below. Other features, objects, and advantages of the invention will be apparent from the description and drawings, and from the claims.

DESCRIPTION OF DRAWINGS

Numbers referring to the same items in several drawings will bear the same reference numbers.

DETAILED DESCRIPTION OF THE PREFERRED EMBODIMENT

The USB interface described below is specifically designed for PD cyclers of the type disclosed in U.S. patent application Ser. No. 11/069,195, filed Feb. 28, 2005, entitled "Portable Apparatus for Peritoneal Dialysis Therapy," Which is incorporated by reference herein in its entirety. In addition, this application hereby incorporates by reference the disclosure in a companion application filed by Kulwinder Plahey the same day as this one, entitled "Improved Cassette System For Peritoneal Dialysis Machine," U.S. patent application Ser. No. 11/515,359, filed Aug. 31, 2006. The foregoing applications are assigned to the same assignee and describe certain details of embodiments of the PD cycler shown in FIG. 1 of the present application.

The Cycler

Figure 1:
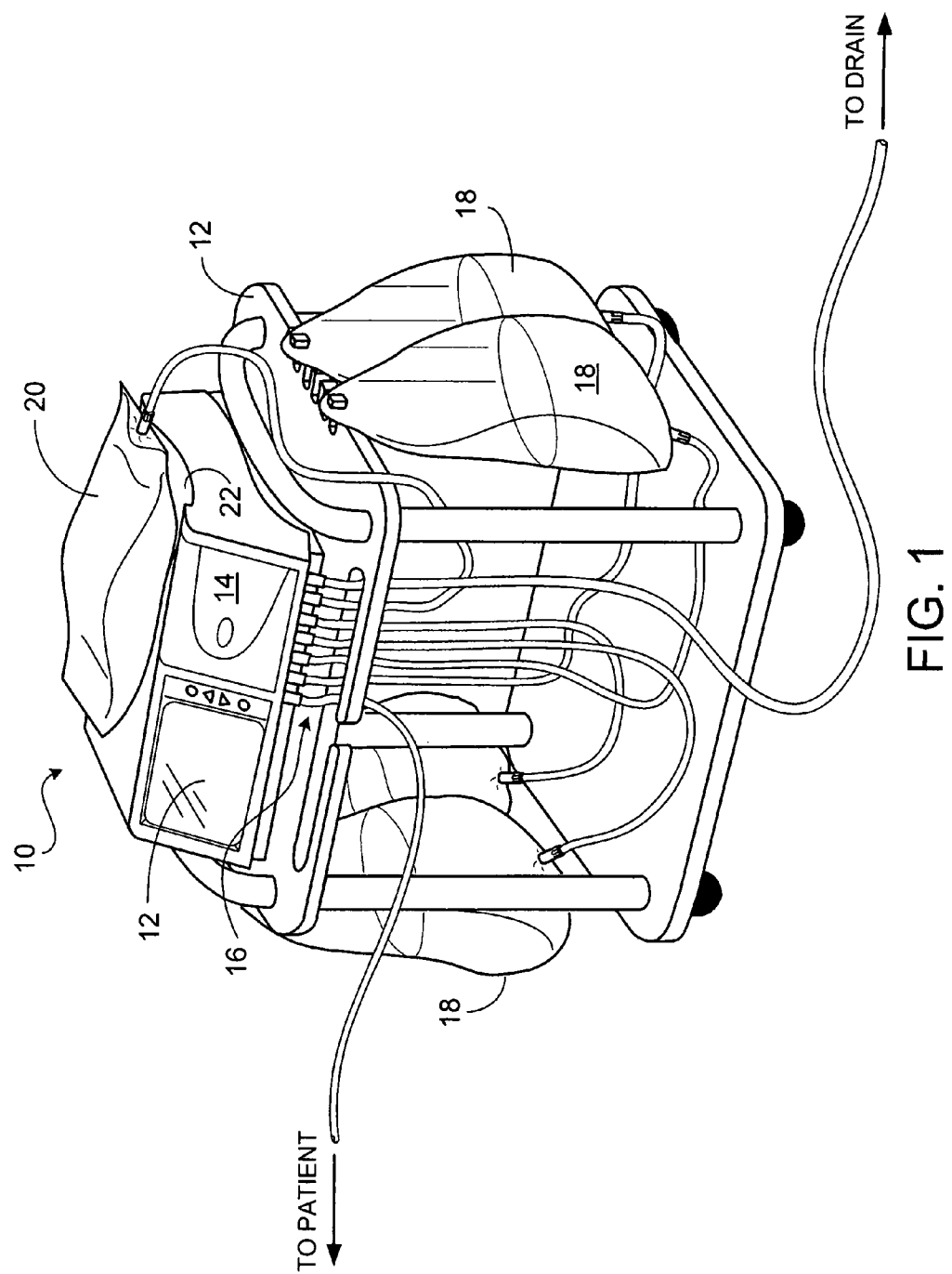
FIG. 1 is a perspective view of a PD cycler on a special cart with a heater bag on the heater tray and additional PD solution bags for more exchanges hanging off the cart.

In FIG. 1, a portable PD cycler 10 is shown seated on top of a cart 12 designed to accommodate the PD solution bags and associated tubing. The front of the cycler 10 includes a control panel 12 that furnishes a user interface designed to be operated by the patient along with a pressurized cassette compartment behind a hinged door 14. The cassette (not shown) includes channels, flexible valve domes and diaphragm covered pumping chambers that are actuated by mating pneumatic valves and pistons interfacing with the cassette compartment to route the flow of PD solution from the bags through the cycler and to the patient and from the patient to a drain. The cassette and cassette compartment are disclosed in more detail in the above-referenced application Ser. No. 11/069,195. The cassette itself has tubing connectors 16 arrayed along its bottom edge. The connectors extend beneath the door 14 and are connected to tubing as shown in FIG. 1.

PD solution bags 18 are suspended from fingers on the sides of the cart 12 as shown. A heater bag 20 is shown lying in a shallow concave depression forming the heater tray 22, which is sized and shaped to accommodate a typical 5 L bag of PD solution. The heater tray 22 has a plurality of heating coils (not shown) embedded below the surface. The surface of the tray 22 is slightly inclined downward to the right to assist in emptying the heater bag which is arranged so that the outlet of the heater bag is also at the right side, adjacent to a temperature sensor 24 positioned in the surface of the heater tray 22 to track the temperature of the solution in the heater bag for a thermostatic control circuit that turns the heating coils on and off as needed to maintain the PD solution at the desired temperature. The heater tray 22 is also mounted internally on a support equipped with a load cell (not shown) to provide an electrical signal indicating the weight of the contents of the PD solution bag to tell the cycler control system how full the heater bag is with PD solution.

The PD cycler has a central programmed microprocessor-based controller for directing the dialysis treatment according to the patient's prescription. This parameter entries, such as number and volume of fills, can be made on the control panel of the PD cycler for a given therapy and the machine will then step through the procedure according to the data entered by the user, in many cases the patient. During the procedure, information concerning cycle times and volumes actually encountered are recorded by the machine and any anomalies or error conditions or alarms generated during the procedure are noted in the record. The system is designed to record the date and time and create a record of the patient's treatment.

There are several instances where the communication of data to and from the PD cycler's control system would be desirable. First, data about the patient can be uploaded. This would include for example the patient's name, ID, age, weight before the procedure and other data about the patient's personal profile, as well as the prescribed treatment. Thus uploading of patient data could simplify the programming of a given treatment and provide a convenient way of monitoring data about the patient.

Second following a treatment, downloading a stored patient record could be beneficial in a number of ways.

What is proposed to accomplish this is a Universal Serial Bus or USB interface that will permit the patient or physician to insert a so-called flash drive memory device with a USB interface into a USB port on the PD cycler in order to upload and download data to and from the PD cycler's control system. This can permit the user to in effect download a "data sheet" following each treatment containing the number of cycles, fill and drain alarms, flow rates, etc., that occurred during the treatment.

On the upload side, the patient would be able to use a simple USB flash drive to enter data into the PD cycler. This data could be stored on any PC. As all PC's have USB ports nowadays, the ease and universality of use is drastically enhanced. Thus the patient might maintain a file on his or her PC with all pertinent patient profile data along with the treatment parameters prescribed by the physician. This file could be maintained current by the patient and could include modifications in prescription made by the physician. In one scenario the physician using a file with a standardized format and adequate security to insure integrity could e-mail the patient a prescription which the patient could then store and transfer to the USB flash drive and then use the USB flash drive to upload the data into the PD cycler. Similarly, the patient could download a data sheet about the treatment from the PD cycler onto his flash drive and then transfer the data sheet to a PC and forward it as an attachment to an e-mail to his physician for inspection and logging as a permanent record.

Figure 2:
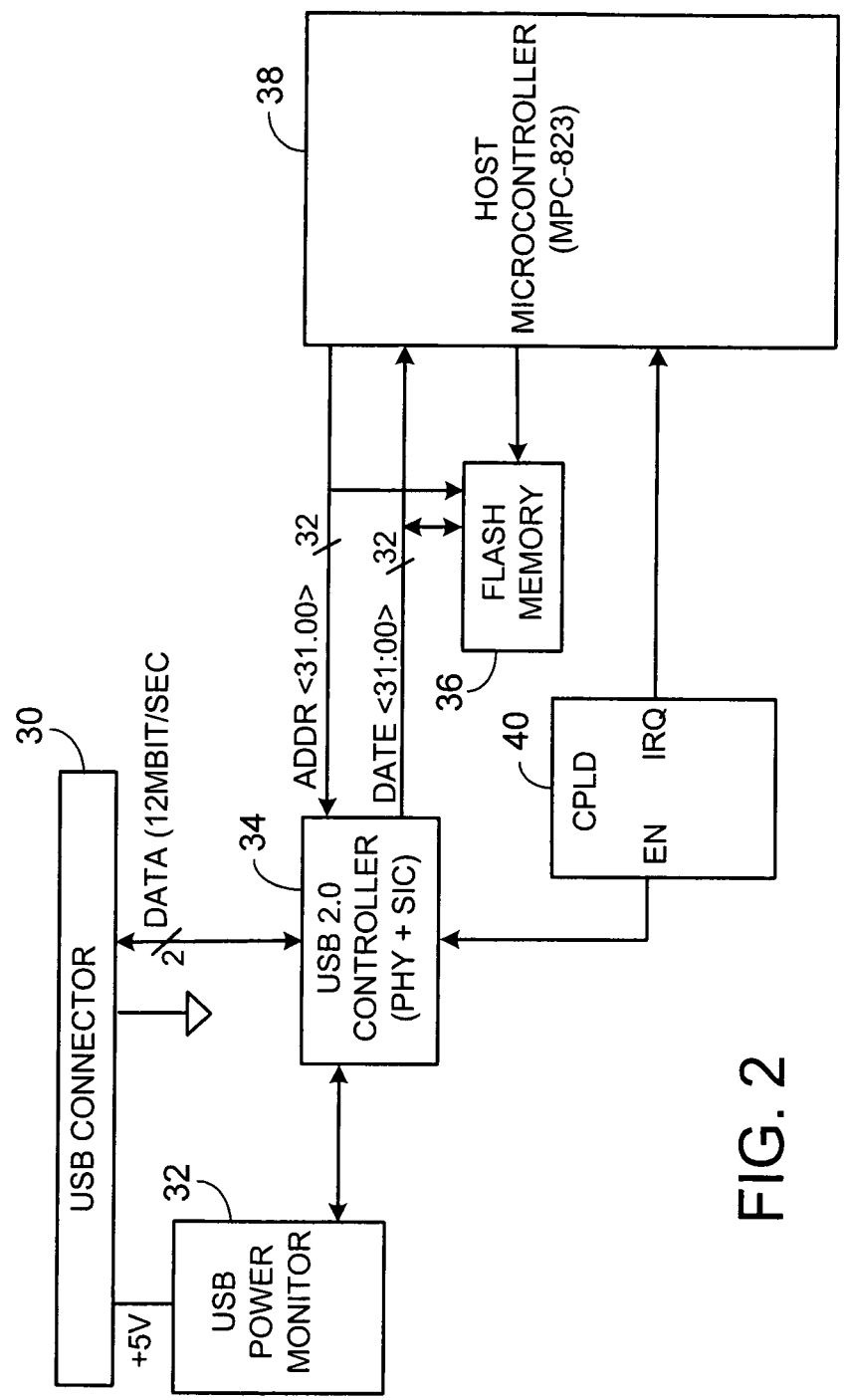
FIG. 2 is a block diagram of the USB interface system within the PD cycler.

The hardware for accomplishing this USB interface is shown in FIG. 2. The USB connector 30 can be implemented by a standard USB 2.0 port located on the back of the PD cycler housing 10 shown in FIG. 1 or any other convenient and safe location on the cycler. The USB connector 30 is connected to a USB 5 volt power monitor 32 and to a USB 2.0 controller 34 via a serial 2-line 12 Mbs data bus. The USB controller 34 detects and establishes communication via a standard protocol with the flash drive or other USB device inserted into the port 30. The controller 34 manages the communication sequence and buffers the data onto or off of the 32 bit address and data lines as shown. The data and addressing lines are connected to a flash memory 36 and the host microcontroller 38 which is preferably a Power PC microprocessor system MPC-823 which is also available to run the other functions of the PD cycler. A complex programmable logic device (CPLD) 40 is connected between the microcontroller 38 and the USB controller to assist in processing data according to the type of data being transmitted.

One of the features of the USB interface for a PD cycler is its potential for uploading playable media files that can be used for training and educational purposes by the user. This can be accomplished by storing a training video on a USB flash drive as an MPEG file, for example. The PD cycler would be equipped with a built in media player. Thus merely by inserting the flash drive into the USB port, the USB controller under the guidance of the CPLD 40 and the microcontroller 38 would automatically unpack and play the training video using the available media player and video drivers for the display 12 on the front of the cycler (FIG. 1). The audio would be played as a wav file on speakers embedded in the cycler. This is a particularly valuable use of the USB interface as it permits the training to take place at home on the users own machine and allows the physician or clinician to prescribe the correct current training video for the patient to use for the particular model of PD cycler that the patient has.

The invention has been described in terms of particular embodiments. Other embodiments are within the scope of the following claims. For example, steps of the invention can be performed in a different order and still achieve desirable results.

What is claimed is:

1. A peritoneal dialysis (PD) machine, comprising:
a source of PD solution;
a PD cycler for routing and delivering the PD solution to a patient in need of peritoneal dialysis;
a controller for directing a sequence of operations on the PD cycler to perform peritoneal dialysis on the patient; and
a USB data communications interface comprising:
a USB port on the machine that accepts a USB memory device; and
a USB interface control system for managing a retrieval of peritoneal dialysis related data from a USB memory device removably disposed in the USB port, the data comprising one or more patient-specific prescription records that are used by the controller to direct the sequence of operations on the PD cycler.

2. The peritoneal dialysis machine of claim 1, wherein the data further comprises an audio visual media file containing a training video specific to the peritoneal dialysis machine.

3. The peritoneal dialysis machine of claim 1, wherein the USB interface control system is configured to write, following a treatment, a digital record of therapy data onto a USB memory device for transfer to a personal computer.

4. The peritoneal dialysis machine of claim 1, wherein the data comprises a patient profile and prescription record provided by a user, the record being stored on a USB memory device and uploaded to the machine via the USB interface.

5. A method performed on a peritoneal dialysis (PD) machine comprising a source of PD solution and a PD cycler for routing and delivering the PD solution to a patient, the method comprising:

receiving, via a USB port on the PD machine, a patient-specific prescription record from a USB memory device removably inserted into the USB port, the patient-specific prescription record comprising one or more treatment parameters transmitted by a physician by way of an electronic messaging system;

directing a sequence of operations on the PD cycler based at least in part on the one or more treatment parameters to perform peritoneal dialysis on the patient;

generating a treatment record based at least in part on the performed peritoneal dialysis; and transferring the treatment record to the USB memory device.

6. The method of claim 5, wherein the treatment record is configured to be attached to an electronic message and transmitted to a physician.

7. The method of claim 5, wherein at least a portion of data contained in the treatment record is usable by a physician to create a modified patient-specific prescription record.

8. The method of claim 5, wherein the one or more treatment records comprise a number of fills.

9. The method of claim 5, wherein the one or more treatment records comprise a volume of fills.

10. The peritoneal dialysis machine of claim 1, wherein the one or more patient-specific prescription records comprise one or more of a user name, a user identification, and a user weight.

* * * * *